United States Patent
James et al.

(10) Patent No.: US 8,388,553 B2
(45) Date of Patent: Mar. 5, 2013

(54) CYCLE AND LOAD MEASUREMENT DEVICE

(75) Inventors: Anthony H. James, Barlett, TN (US); Sied W. Janna, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 990 days.

(21) Appl. No.: 11/718,588

(22) PCT Filed: Nov. 4, 2005

(86) PCT No.: PCT/US2005/040052
§ 371 (c)(1),
(2), (4) Date: Jul. 19, 2007

(87) PCT Pub. No.: WO2006/052765
PCT Pub. Date: May 18, 2006

(65) Prior Publication Data
US 2008/0208516 A1    Aug. 28, 2008

Related U.S. Application Data (60) Provisional application No. 60/625,019, filed on Nov. 4, 2004.

(51) Int. Cl.
*A61B 5/103* (2006.01)
*A61B 5/117* (2006.01)
(52) U.S. Cl. ........................ 600/587; 600/595
(58) Field of Classification Search ............ 600/587, 600/595; 623/16.11, 914
See application file for complete search history.

(56) References Cited

U.S. PATENT DOCUMENTS

| | | | |
|---|---|---|---|
| 3,713,148 A | 1/1973 | Cardullo et al. | |
| 3,727,209 A * | 4/1973 | White et al. | 307/116 |
| 3,976,060 A | 8/1976 | Hildebrandt et al. | |
| 4,096,477 A | 6/1978 | Epstein et al. | |
| 4,242,663 A | 12/1980 | Slobodin | |
| 4,281,664 A | 8/1981 | Duggan | |
| 4,361,153 A | 11/1982 | Slocum et al. | |
| 4,441,498 A | 4/1984 | Nordling | |
| 4,473,825 A | 9/1984 | Walton | |
| 4,481,428 A | 11/1984 | Charlot | |

(Continued)

FOREIGN PATENT DOCUMENTS

| | | |
|---|---|---|
| DE | 19855254 A1 | 6/2000 |
| EP | 62459 A2 | 9/1983 |

(Continued)

OTHER PUBLICATIONS

Burny, et al., "Smart orthopedic implants", Orthopedics, Dec. 2005; 28 (12):1401.

(Continued)

*Primary Examiner* — Rene Towa
(74) *Attorney, Agent, or Firm* — Fish & Richardson P.C.

(57) ABSTRACT

The present application relates to a sensing system for an medical device, the sensing system having at least one sensor for measuring movement of the medical device and a recording device for storing movement data from the at least one sensor. The application also relates to a method for evaluating a patient's compliance with a healing regimen, the patient provided with a medical device, the method having the steps of a) collecting movement data relating to movement of a sensing system affixed within, to, or near the medical device; b) retrieving the movement data from the sensing system; and c) analyzing the movement data and comparing the movement data to standard movement data to evaluate the patient's compliance with the healing regimen.

41 Claims, 5 Drawing Sheets

U.S. PATENT DOCUMENTS

| | | |
|---|---|---|
| 4,494,545 A | 1/1985 | Slocum et al. |
| 4,510,495 A | 4/1985 | Sigrimis et al. |
| 4,513,743 A | 4/1985 | van Arragon et al. |
| 4,525,713 A | 6/1985 | Barletta et al. |
| 4,546,241 A | 10/1985 | Walton |
| 4,571,589 A | 2/1986 | Slocum et al. |
| 4,576,158 A | 3/1986 | Boland |
| 4,944,299 A | 7/1990 | Silvian |
| 4,952,928 A | 8/1990 | Carroll et al. |
| 4,991,682 A * | 2/1991 | Kuntz et al. ................ 180/282 |
| 5,022,439 A | 6/1991 | Yano et al. |
| 5,024,239 A | 6/1991 | Rosenstein |
| 5,030,236 A | 7/1991 | Dean |
| 5,042,504 A * | 8/1991 | Huberti ..................... 600/592 |
| 5,117,825 A | 6/1992 | Grevious |
| 5,197,488 A | 3/1993 | Kovacevic |
| 5,252,962 A | 10/1993 | Urbas et al. |
| 5,309,919 A | 5/1994 | Snell et al. |
| 5,326,363 A | 7/1994 | Aikins |
| 5,330,477 A | 7/1994 | Crook |
| 5,334,202 A | 8/1994 | Carter |
| 5,337,747 A | 8/1994 | Neftel |
| 5,360,016 A | 11/1994 | Kovacevic |
| 5,383,935 A | 1/1995 | Shirkhanzadeh |
| 5,481,262 A | 1/1995 | Urbas et al. |
| 5,416,695 A | 5/1995 | Stutman et al. |
| 5,423,334 A | 6/1995 | Jordan |
| 5,425,775 A | 6/1995 | Kovacevic et al. |
| 5,456,724 A | 10/1995 | Yen et al. |
| 5,470,354 A | 11/1995 | Hershberger et al. |
| 5,518,008 A | 5/1996 | Cucchiaro et al. |
| 5,524,637 A | 6/1996 | Erickson |
| 5,533,519 A | 7/1996 | Radke et al. |
| 5,626,630 A | 5/1997 | Markowitz et al. |
| 5,630,835 A | 5/1997 | Brownlee |
| 5,681,313 A | 10/1997 | Diez |
| 5,695,496 A | 12/1997 | Orsak et al. |
| 5,720,746 A | 2/1998 | Soubeiran |
| 5,733,292 A | 3/1998 | Gustilo et al. |
| 5,735,887 A | 4/1998 | Barreras et al. |
| 5,741,315 A | 4/1998 | Lee et al. |
| 5,792,076 A | 8/1998 | Orsak et al. |
| 5,807,701 A | 9/1998 | Payne et al. |
| 5,833,603 A | 11/1998 | Kovacs et al. |
| 5,836,989 A | 11/1998 | Shelton |
| 5,873,843 A | 2/1999 | Draper |
| 5,904,708 A | 5/1999 | Goedeke |
| 5,935,171 A | 8/1999 | Schneider et al. |
| 5,944,745 A | 8/1999 | Rueter |
| 6,009,878 A | 1/2000 | Weijand et al. |
| 6,025,725 A | 2/2000 | Gershenfeld et al. |
| 6,034,295 A | 3/2000 | Rehberg et al. |
| 6,034,296 A * | 3/2000 | Elvin et al. ................ 623/16.11 |
| 6,059,576 A * | 5/2000 | Brann ......................... 434/247 |
| 6,061,597 A * | 5/2000 | Rieman et al. ................... 607/51 |
| 6,102,874 A | 8/2000 | Stone et al. |
| 6,111,520 A | 8/2000 | Allen et al. |
| 6,120,502 A | 9/2000 | Michelson |
| 6,135,951 A | 10/2000 | Richardson et al. |
| 6,143,035 A | 11/2000 | McDowell |
| 6,168,569 B1 | 1/2001 | McEwen et al. |
| 6,183,425 B1 * | 2/2001 | Whalen et al. ................ 600/592 |
| 6,200,265 B1 | 3/2001 | Walsh et al. |
| 6,201,980 B1 | 3/2001 | Darrow et al. |
| 6,210,301 B1 | 4/2001 | Abraham-Fuchs et al. |
| 6,245,109 B1 | 6/2001 | Mendes et al. |
| 6,312,612 B1 | 11/2001 | Sherman et al. |
| 6,325,756 B1 | 12/2001 | Webb et al. |
| 6,327,501 B1 | 12/2001 | Levine et al. |
| 6,356,789 B1 | 3/2002 | Hinssen et al. |
| 6,369,694 B1 | 4/2002 | Mejia |
| 6,385,593 B2 | 5/2002 | Linberg |
| 6,402,689 B1 | 6/2002 | Scarantino et al. |
| 6,433,629 B2 | 8/2002 | Hamel et al. |
| 6,434,429 B1 | 8/2002 | Kraus et al. |
| 6,442,432 B2 | 8/2002 | Lee |
| 6,447,448 B1 | 9/2002 | Ishikawa et al. |
| 6,447,449 B1 | 9/2002 | Fleischman et al. |
| 6,449,508 B1 * | 9/2002 | Sheldon et al. ................ 607/19 |
| 6,466,810 B1 | 10/2002 | Ward et al. |
| 6,477,424 B1 | 11/2002 | Thompson et al. |
| 6,482,154 B1 | 11/2002 | Haubrich et al. |
| 6,497,655 B1 | 12/2002 | Linberg et al. |
| 6,499,488 B1 * | 12/2002 | Hunter et al. ................ 128/899 |
| 6,527,711 B1 | 3/2003 | Stivoric et al. |
| 6,529,127 B2 | 3/2003 | Townsend et al. |
| 6,535,766 B1 | 3/2003 | Thompson et al. |
| 6,539,253 B2 | 3/2003 | Thompson et al. |
| 6,553,262 B1 | 4/2003 | Lang et al. |
| 6,567,703 B1 | 5/2003 | Thompson et al. |
| 6,573,706 B2 | 6/2003 | Mendes et al. |
| 6,583,630 B2 | 6/2003 | Mendes et al. |
| 6,602,191 B2 | 8/2003 | Quy |
| 6,610,096 B2 | 8/2003 | MacDonald |
| 6,636,769 B2 | 10/2003 | Govari et al. |
| 6,638,231 B2 | 10/2003 | Govari et al. |
| 6,641,540 B2 | 11/2003 | Fleischman et al. |
| 6,652,464 B2 | 11/2003 | Schwartz et al. |
| 6,658,300 B2 | 12/2003 | Govari et al. |
| 6,667,725 B1 | 12/2003 | Simons et al. |
| 6,675,044 B2 | 1/2004 | Chen |
| 6,682,490 B2 | 1/2004 | Roy et al. |
| 6,694,180 B1 | 2/2004 | Boesen |
| 6,706,005 B2 | 3/2004 | Roy et al. |
| 6,712,778 B1 * | 3/2004 | Jeffcoat et al. ................ 600/590 |
| 6,738,671 B2 | 5/2004 | Christophersom et al. |
| 6,749,568 B2 | 6/2004 | Fleischman et al. |
| 6,753,778 B2 * | 6/2004 | Kruger ......................... 340/568.6 |
| 6,764,446 B2 | 7/2004 | Wolinsky et al. |
| 6,766,200 B2 | 7/2004 | Cox |
| 6,783,499 B2 | 8/2004 | Schwartz |
| 6,790,372 B2 | 9/2004 | Roy et al. |
| 6,793,659 B2 | 9/2004 | Putnam |
| 6,804,552 B2 | 10/2004 | Thompson et al. |
| 6,807,439 B2 | 10/2004 | Edwards et al. |
| 6,810,753 B2 | 11/2004 | Valdevit et al. |
| 6,819,247 B2 | 11/2004 | Birnbach et al. |
| 6,821,299 B2 | 11/2004 | Kirking et al. |
| 6,834,436 B2 | 12/2004 | Townsend et al. |
| 6,855,115 B2 | 2/2005 | Fonseca et al. |
| 6,864,802 B2 | 3/2005 | Smith et al. |
| 6,895,280 B2 | 5/2005 | Meadows et al. |
| 6,895,281 B1 | 5/2005 | Amundson et al. |
| 6,926,670 B2 | 8/2005 | Rich et al. |
| 6,939,299 B1 | 9/2005 | Petersen et al. |
| 6,968,743 B2 | 11/2005 | Rich et al. |
| 6,994,672 B2 | 2/2006 | Fleischman et al. |
| 7,001,346 B2 | 2/2006 | White |
| 7,027,871 B2 | 4/2006 | Burnes et al. |
| 7,034,694 B2 | 4/2006 | Yamaguchi et al. |
| 7,097,662 B2 | 8/2006 | Evans et al. |
| 7,145,461 B2 | 12/2006 | Lehrman et al. |
| 7,147,604 B1 | 12/2006 | Allen et al. |
| 7,151,914 B2 | 12/2006 | Brewer |
| 7,182,736 B2 | 2/2007 | Roy et al. |
| 7,190,273 B2 | 3/2007 | Liao et al. |
| 7,195,645 B2 | 3/2007 | Disilvestro et al. |
| 7,209,790 B2 | 4/2007 | Thompson et al. |
| 7,212,133 B2 | 5/2007 | Goetz et al. |
| 7,218,232 B2 | 5/2007 | DiSilvestro et al. |
| 7,229,415 B2 | 6/2007 | Schwartz |
| 7,256,695 B2 | 8/2007 | Hamel et al. |
| 7,333,013 B2 | 2/2008 | Berger |
| 7,357,037 B2 | 4/2008 | Hnat et al. |
| 7,474,223 B2 | 1/2009 | Nycz et al. |
| 7,559,951 B2 | 7/2009 | DiSilvestro et al. |
| 7,756,579 B2 | 7/2010 | Nitzan et al. |
| 7,780,613 B2 | 8/2010 | Sherman |
| 8,007,450 B2 | 8/2011 | Williams |
| 2001/0047125 A1 | 11/2001 | Quy |
| 2002/0099359 A1 | 7/2002 | Santini et al. |
| 2002/0116080 A1 | 8/2002 | Birnbach et al. |
| 2002/0138153 A1 | 9/2002 | Koniuk |
| 2002/0151978 A1 | 10/2002 | Zacouto et al. |
| 2002/0170193 A1 | 11/2002 | Townsend et al. |
| 2003/0040806 A1 | 2/2003 | MacDonald |
| 2003/0069644 A1 | 4/2003 | Kovacevic et al. |

| Publication Number | Date | Inventor |
|---|---|---|
| 2003/0105470 A1 | 6/2003 | White |
| 2003/0120150 A1 | 6/2003 | Govari |
| 2003/0136417 A1 | 7/2003 | Fonseca et al. |
| 2003/0143775 A1 | 7/2003 | Brady |
| 2003/0178488 A1 | 9/2003 | Southard |
| 2003/0229381 A1 | 12/2003 | Hochmair et al. |
| 2004/0008123 A1 | 1/2004 | Carrender et al. |
| 2004/0011137 A1 | 1/2004 | Hnat et al. |
| 2004/0014456 A1 | 1/2004 | Väänänen |
| 2004/0019382 A1 | 1/2004 | Amirouche et al. |
| 2004/0073137 A1 | 4/2004 | Lloyd et al. |
| 2004/0073221 A1 | 4/2004 | Biscup |
| 2004/0094613 A1* | 5/2004 | Shiratori et al. ............. 235/105 |
| 2004/0113790 A1 | 6/2004 | Hamel et al. |
| 2004/0116837 A1 | 6/2004 | Yamaguchi et al. |
| 2004/0152972 A1 | 8/2004 | Hunter |
| 2004/0077073 A1 | 9/2004 | Xie et al. |
| 2004/0176815 A1 | 9/2004 | Janzig et al. |
| 2004/0186396 A1 | 9/2004 | Roy et al. |
| 2004/0204647 A1 | 10/2004 | Grupp et al. |
| 2004/0231420 A1 | 11/2004 | Xie et al. |
| 2004/0243148 A1* | 12/2004 | Wasielewski ................. 606/130 |
| 2004/0249315 A1* | 12/2004 | Damen ......................... 600/595 |
| 2005/0010139 A1 | 1/2005 | Aminian et al. |
| 2005/0010299 A1* | 1/2005 | Disilvestro ................. 623/18.12 |
| 2005/0010300 A1 | 1/2005 | Disilvestro et al. |
| 2005/0010301 A1 | 1/2005 | Disilvestro et al. |
| 2005/0010302 A1 | 1/2005 | Dietz et al. |
| 2005/0012610 A1 | 1/2005 | Liao et al. |
| 2005/0012617 A1* | 1/2005 | DiSilvestro et al. ....... 340/572.8 |
| 2005/0015014 A1 | 1/2005 | Fonseca et al. |
| 2005/0061079 A1 | 3/2005 | Schulman |
| 2005/0099290 A1 | 5/2005 | Govari |
| 2005/0101833 A1 | 5/2005 | Hsu et al. |
| 2005/0113932 A1 | 5/2005 | Kovacevic |
| 2005/0131397 A1 | 6/2005 | Levin |
| 2005/0187482 A1 | 8/2005 | O'Brien et al. |
| 2005/0194174 A1 | 9/2005 | Hipwell et al. |
| 2005/0234555 A1 | 10/2005 | Sutton et al. |
| 2005/0247319 A1 | 11/2005 | Berger |
| 2005/0273170 A1* | 12/2005 | Navarro et al. ............ 623/17.13 |
| 2005/0288727 A1 | 12/2005 | Penner |
| 2006/0009856 A1 | 1/2006 | Sherman et al. |
| 2006/0030771 A1 | 2/2006 | Levine et al. |
| 2006/0032314 A1 | 2/2006 | Hnat et al. |
| 2006/0043178 A1 | 3/2006 | Tethrake et al. |
| 2006/0043179 A1 | 3/2006 | Nycz et al. |
| 2006/0047283 A1* | 3/2006 | Evans et al. .................... 606/102 |
| 2006/0052782 A1 | 3/2006 | Morgan et al. |
| 2006/0058627 A1 | 3/2006 | Flaherty et al. |
| 2006/0065739 A1 | 3/2006 | Falls et al. |
| 2006/0069436 A1 | 3/2006 | Sutton et al. |
| 2006/0069447 A1 | 3/2006 | DiSilvestro et al. |
| 2006/0109105 A1 | 5/2006 | Varner et al. |
| 2006/0111291 A1 | 5/2006 | DiMauro et al. |
| 2006/0119481 A1 | 6/2006 | Tethrake et al. |
| 2006/0142656 A1 | 6/2006 | Malackowski et al. |
| 2006/0145871 A1 | 7/2006 | Donati et al. |
| 2006/0174712 A1 | 8/2006 | O'Brien et al. |
| 2006/0177956 A1 | 8/2006 | O'Brien et al. |
| 2006/0190080 A1 | 8/2006 | Danoff et al. |
| 2006/0196277 A1 | 9/2006 | Allen et al. |
| 2006/0200030 A1 | 9/2006 | White et al. |
| 2006/0200031 A1 | 9/2006 | White et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0260401 A1 | 11/2006 | Xie |
| 2006/0271199 A1 | 11/2006 | Johnson |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0038051 A1 | 2/2007 | Talman et al. |
| 2007/0078497 A1 | 4/2007 | Vandanacker |
| 2007/0089518 A1 | 4/2007 | Ericson et al. |
| 2007/0090543 A1 | 4/2007 | Condie et al. |
| 2007/0100215 A1 | 5/2007 | Powers et al. |
| 2007/0129769 A1 | 6/2007 | Bourget et al. |
| 2007/0180922 A1 | 8/2007 | Crottet et al. |
| 2007/0208544 A1 | 9/2007 | Kulach et al. |
| 2007/0219639 A1 | 9/2007 | Otto et al. |
| 2008/0086145 A1 | 4/2008 | Sherman et al. |
| 2008/0105874 A1 | 5/2008 | Wang et al. |
| 2008/0161729 A1 | 7/2008 | Bush |
| 2008/0300597 A1 | 12/2008 | Morgan et al. |
| 2009/0131838 A1 | 5/2009 | Fotiadis et al. |
| 2009/0222050 A1 | 9/2009 | Wolter et al. |
| 2010/0152621 A1 | 6/2010 | Janna et al. |

FOREIGN PATENT DOCUMENTS

| | | |
|---|---|---|
| EP | 987047 A2 | 3/2000 |
| EP | 1023872 A2 | 8/2000 |
| EP | 1099415 A1 | 5/2001 |
| EP | 959956 B1 | 12/2001 |
| EP | 1256316 A | 11/2002 |
| EP | 1256316 A1 | 11/2002 |
| EP | 1309960 B1 | 6/2004 |
| EP | 1331903 B1 | 6/2004 |
| EP | 1502540 A1 | 2/2005 |
| EP | 1570781 A1 | 9/2005 |
| EP | 1570782 A2 | 9/2005 |
| EP | 1586287 A2 | 10/2005 |
| EP | 1541095 A3 | 1/2006 |
| EP | 1611835 A2 | 1/2006 |
| EP | 1642550 A2 | 4/2006 |
| EP | 1366712 A1 | 5/2006 |
| EP | 1535039 A4 | 8/2006 |
| EP | 1738716 A2 | 1/2007 |
| EP | 1765204 | 3/2007 |
| EP | 1377340 B1 | 5/2007 |
| EP | 1803394 A2 | 7/2007 |
| EP | 1830303 A1 | 9/2007 |
| EP | 1582183 B1 | 8/2009 |
| EP | 1495456 B1 | 8/2010 |
| EP | 1765204 A4 | 3/2012 |
| WO | WO8200378 A | 2/1982 |
| WO | WO9006720 A1 | 6/1990 |
| WO | WO9621397 A1 | 7/1996 |
| WO | WO9626678 A1 | 9/1996 |
| WO | WO9629007 | 9/1996 |
| WO | WO 9629007 A | 9/1996 |
| WO | WO9714367 A1 | 4/1997 |
| WO | WO9720512 A1 | 6/1997 |
| WO | WO9843701 A1 | 10/1998 |
| WO | WO0030534 A1 | 6/2000 |
| WO | WO0032124 A1 | 6/2000 |
| WO | WO0137733 A2 | 5/2001 |
| WO | WO0119248 A8 | 6/2001 |
| WO | WO0018317 A9 | 7/2001 |
| WO | WO0203347 A1 | 1/2002 |
| WO | WO0238082 A1 | 5/2002 |
| WO | WO0019888 A9 | 8/2002 |
| WO | WO02061705 A | 8/2002 |
| WO | WO02061705 A1 | 8/2002 |
| WO | WO02058551 A3 | 10/2002 |
| WO | WO02056763 A3 | 11/2002 |
| WO | WO 03/008570 | 1/2003 |
| WO | WO03003145 A3 | 3/2003 |
| WO | WO03044556 A2 | 5/2003 |
| WO | WO03085617 A1 | 10/2003 |
| WO | WO2004005872 A2 | 1/2004 |
| WO | WO2004052453 A1 | 6/2004 |
| WO | WO2004052456 A1 | 6/2004 |
| WO | WO2004077073 A1 | 6/2004 |
| WO | WO2004077073 A1 | 9/2004 |
| WO | WO2004014456 A3 | 12/2004 |
| WO | WO2005013851 A2 | 2/2005 |
| WO | WO2005039440 A2 | 5/2005 |
| WO | WO2005074821 A | 8/2005 |
| WO | WO 2005074821 A2 | 8/2005 |
| WO | WO 2005084544 A1 | 9/2005 |
| WO | WO2005104997 A2 | 11/2005 |
| WO | WO2005120203 A2 | 12/2005 |
| WO | WO2005007025 A3 | 1/2006 |
| WO | WO 2006010037 A2 | 1/2006 |
| WO | WO 2006/045080 | 4/2006 |
| WO | WO2006045607 A1 | 5/2006 |
| WO | WO2006055547 A2 | 5/2006 |

| | | |
|---|---|---|
| WO | WO 2006/063156 | 6/2006 |
| WO | WO2006052765 A3 | 8/2006 |
| WO | WO2006086113 A2 | 8/2006 |
| WO | WO2006089069 A2 | 8/2006 |
| WO | WO2006096582 A1 | 9/2006 |
| WO | WO2006049796 A3 | 10/2006 |
| WO | WO2006110798 A2 | 10/2006 |
| WO | WO2006113660 A1 | 10/2006 |
| WO | WO2006094273 A3 | 1/2007 |
| WO | WO2007002185 A2 | 1/2007 |
| WO | WO2007002224 A2 | 1/2007 |
| WO | WO2007002225 A2 | 1/2007 |
| WO | WO2007008493 A1 | 1/2007 |
| WO | WO2007009088 A1 | 1/2007 |
| WO | WO 2007025191 A1 | 3/2007 |
| WO | WO2007030489 A1 | 3/2007 |
| WO | WO2007036318 A1 | 4/2007 |
| WO | WO2007041124 A1 | 4/2007 |
| WO | WO2006086114 A3 | 5/2007 |
| WO | WO2007061890 A2 | 5/2007 |
| WO | WO2007090543 A1 | 8/2007 |
| WO | WO2008105874 A1 | 9/2008 |
| WO | WO 2009/098768 | 8/2009 |

OTHER PUBLICATIONS

Rydell, "Forces Acting on the Femoral Head Prosthesis", Acta Orthop Scand, Suppl. 88, 1966.

Lanyon, et al., "In Vivo Strain Measurements from Bone and Prosthesis following Total Hip Replacement", The Journal of Bone and Joint Surgery, vol. 63-A, No. 6, pp. 989-1000,1981.

Carlson, et al., "A Radio Telemetry Device for Monitoring Cartilage Surface Pressures in the Human Hip", IEEE Trans. on Biomed. Engrg., vol. BME-21, No. 4, pp. 257-264, Jul. 1974.

Carlson, et all, "A look at the prosthesis-cartilage interface: design of a hip prosthesis containing pressure transducers.", J Biomed Mater Res. 1974; 8(4 pt 2): 261-269.

English, et al., In vivo records of hip loads using a femoral implant with telemetric output (a preliminary report), J Biomed Eng. 1979; 1:111-115.

Rushfeldt, et al., Improvd Techniques for Measuring in Vitro Geometry and Pressure Distribution in Human Acetabulum-II. Instrumented . . . J Biomechanics No. 14, pp. 315-323, 1981.

Hodge, et al., "Preliminary in Vivo Pressure Measurements in a Human Acetabulum", Proceedings of 31st Annual Meeting, Orthopaedic Research Society, 1985.

Hodge, et al., "Contact Pressures in the Human Hip Joint Measured in Vivo", Proc. of National Academy of Science, U.S.A., No. 83, pp. 2879-2883, 1986.

Brown, et al., "In Vivo Load Measurements on a Total Hip Prosthesis", Proceedings of the 31st Meeting, Orthopaedic Research Society, 1985.

Davy, et al., "Telemetric Force Measurements across the Hip after Total Arthroplasty", Journal of Bone and Joint Surgery, vol. 70-A, No. 1, Jan. 1988: 45-50.

Taylor, et al., "Telemetry of forces from proximal femoral replacements and relevance to fixation", J Biomech. 1997; 30:225-234.

Bergmann, et al., "Multichannel Strain Gauge Telemetry for Orthopaedic Implants", Technical Note, J. Biomechanics, vol. 21, No. 2, pp. 169-176, 1988.

Rohlmann, et al., "Telemeterized Load Measurement Using Instrumented Spinal Internal Fixators in a Patient with Degenerative Instability", Spine, vol. 20, No. 24, 1995.

Berkman, et al., "Biomedical Micropressor with Analog I/O", Inter. Solid-State Circuits Conf. Cigest of Technical Papers, pp. 168-169, 1981.

Dorman, et al., "A Monolithic Signal Processor for a Neurophysiological Telemetry System", IEEE Journal of Solid-State Circuits, vol. 20, pp. 1185-1193, 1985.

Gschwend, et al., "A General Purpose Implantable Multichannel Telemetry System for Physiological Research", Biotelemetry Patient Monitoring, vol. 6, pp. 107-117, 1979.

Cook, et al., "A Custom Microprocessor for Implantable Telemetry Systems", Proc of the IEEE Symp. on Computer-Based Medical Systems, pp. 412-417, Jun. 1990.

Brown, et al., "Telemetering in vivo loads from nail plate Implants", J. Biomechanics, vol. 15, No. 11, pp. 815-823, 1982.

Fernald, et al., "A System Architecture for Intelligent Implantable Biotelemetry Instruments", Proc. IEEE Eng in Medicine and Biology Soc. Annual Conf., pp. 1411-1412 1989.

Rohlmann, et al., "Influence of load carrying on loads in internal spinal fixators", J Biomech. 2000; 33:1099-1104.

Rohlmann, et al., "Loads on an internal spinal fixation device during walking", J Biomech. 1997; 30:41-47.

Schneider, et al, "Loads acting in an intramedullary nail during fracture healing in the human femur", Journal of Biomechanics 34, 2001, pp. 849-857.

Heinlein, et al., "An instrumented knee endoprosthesis for measuring loads in vivo", EORS 2004, 51st Annual Meeting.

Townsend, et al., "Multichannel, Programmable, Microprocessor Based Strain Gauge . . . ", 18th Ann. Int Conf. IEEE Eng. in Med & Biology Soc. Oct. 31-Nov. 3, 1996, Amsterdam.

Mendes, et al., "IntelliJoint System for monitoring displacement in biologic system", Biomed Bytes 2002 (4), pp. 69-70.

Crisstofolini, et al., "A novel transducer for the measurement of cement-prosthesis interface forces in cemented . . . " , Medicial Eng & Physics vol. 22, 7, Sep. 2000, pp. 493-501.

Müller, et al., "Three-dimensional measurements of the pressure distribution in articicial joints with a capacitive sensor array", J Biomech, vol. 37, Oct. 2004, pp. 1623-1625.

Bergmann, et al., "Frictional heating of total hip implants, Part 1: measurements in patients" Journal of Biomechanics, vol. 34, Issue 4, Apr. 2001, pp. 421-428.

Rohlmann, et al., "In vitro load measurement using an instrumented spinal fixation device", Medical Engineering & Physics, vol. 18, Issue 6, Sep. 1996, pp. 485-488.

Burny, et al., "Concept, design and fabrication of smart orthopaedic implants", Medical Engineering & Physics, 22 (2000), pp. 469-479.

D'Lima, et al., "An implantable telemetry device to measure intra-articular tibial forces", J Biomech. Feb. 2005;38(2): pp. 299-304.

Bergmann, et al., "Hip joint contact forces during stumbling", Langenbecks Arch Surg. Feb. 2004; 389(1): 53-9. Epub Nov. 19, 2003.

Stansfield, et al., "Direct comparison of calculated hip joint contact forces with those measured using instrumented implants . . . " J Biomech. Jul. 2003;36(7):929-36.

Heller, et al., "Musculo-skeletal loading conditions at the hip during walking and stair climbing", J Biomech. Jul. 2001; 34(7):883-93.

Bergmann, et al., "Hip contact forces and gait patterns from routing activities", J. Biomech. Jul. 2001;34(7):859-71.

Bergmann, et al., "Frictional heating of total hip implants", Part 2: finite element study. J Biomech. Apr. 2001;34(4):429-35.

Park, et al, "Hip muscle co-contraction: evidence from concurrent in vivo pressure measurement and force estimation", Gait Posture. Dec. 1999;10(3):211-22.

Graichen, et al., "Hip endoprosthesis for in vivo measurement of joint force and temperature", J Biomech. Oct. 1999;32(10):1113-7.

Krebs, et al., "Hip biomechanics during gait", J Orthop & Sports Phys Ther. Jul. 1998;28(1):51-9.

Tackson, et al., "Acetabular pressures during hip arthritis exercises", Arthritis Care & Res. Oct. 1997;10(5):308-19.

Kotzar, et al, "Torsional loads in the early postoperative period following total hip replacement", J Orthop Res. Nov. 1995;13(6):945-55.

Bergmann, et al, Is staircase walking a risk for the fixation of hip implants?, J Biomech, May 1995; 28(5):535-53.

Brand, et al, "Comparison of hip force calculations and measurements in the same patient", J Arthroplasty, Feb. 1994;9(1):45-51.

Bergmann, et al., "Hip joint loading during walking and running, measured in two patients", J Biomech, Aug. 1993;26(8):969-90.

Graichen, et al., "Four-channel telemetry system for in vivo measurement of hip joint forces", J Bioment Eng, Sep. 1991;13(5):370-4.

Kotzar, et al., "Telemeterized in vivo hip joint force data: a report on two patients after total hip surgery", J Orthop Res., Sep. 1991;9(5):621-33.

Morrell, et al., "Corroboration of in vivo cartilage pressures with implacations for synovial joint tribology and . . . ", Proc Natl Acad Sci USA, Oct. 11, 2005; 102(41):14819-24.

McGibbon, et al., "Cartilage degeneration in relation to repetitive pressure: case study of a unilateral hip hemiarthroplasty patient", J Arthroplasty, Jan. 1999;14(1):52-8.

Lu, et al., "Influence of muscle activity on the forces in the femur: an in vivo study", J Biomech, Nov.-Dec. 1997;30(11-12):1101-6.

Taylor, et al., "Telemetry of forces from proximal femoral replacements and relevance to fixation", J Biomech, Mar. 1997;30(3):225-34.

Puers, et al., "A telemetry system for the detection of hip prosthesis loosening by vibration analysis", Sensors and Actuators 85 (2000) 42-47.

Fruin, et al, "Validity of a Multi-Sensor Armband in Estimating Rest and Exercise Energy Expenditure", Am Coll Sports Med, vol. 36, 6, pp. 1063-1069, 2004.

Jakicic, et al, "Evaluation of the SenseWear Pro Armband™ to Assess Energy Expenditure during Exercise", Med. Sci. Sports Exerc.; vol. 36,5, pp. 897-904, 2004.

Nachemson et al., "Intravital wireless telemetry of axial forces in Harrington distraction rods in patients with idiopathic scoliosis", J.Bone Jt Surg. 53A, 445-464 (Apr. 1971).

Townsend, et al., "'Remotely powered multichannel microprocessor based telemetry systemsfor smart implantable devices and smart structures,'" Proc. SPIE vol. 3673, pp. 150-156 (Mar. 1999).

Aminian K, et al., "Temporal Feature Estimation During Walking Using Miniature Accelerometers . . . " Med Biol Eng Comput, 1999, 37, 686-691.

Bussmann JBJ, et al., "Analysis and Decomposition of Signals Obtained by Thigh-Fixed Uni-Axial Accelerometry During Normal Walking," Med Biol Eng Comput, 2000, 38, 632-638.

Petrofsky JS, et al., "Joint Acceleration during Gait in Relation to Age," Eur J Appl Physiology. 2004, 92: 254-262.

Patent Application for U.S. Appl. No. 60/710,550, filed Aug. 23, 2005.

International Search Report and Written Opinion for International Application PCT/US2006/033326 dated Dec. 13, 2005, 9 pages.

International Search Report and Written Opinion for International Application PCT/US2007/062757 dated Nov. 19, 2007, 8 pages.

International Search Report for International Application PCT/US2008/075316 dated Dec. 3, 2008, 2 pages.

International Search Report and Written Opinion for International Application PCT/US2008/032540 dated Apr. 29, 2009, 7 pages.

International Preliminary Report on Patentability for International Application No. PCT/US2007/062757, mailed Aug. 29, 2009, 6 pages.

International Preliminary Report on Patentability for International Application No. PCT/US2008/075316, mailed Mar. 9, 2010, 7 pages.

Bergmann, et al, "Design and Calibration of Load Sensing Orthopaedic Implants," Journal of Biomechanical Engineering, Apr. 2008, vol. 130, 9 pages.

Catrysse, M., et al., "An Inductive Powering System with Integrated Bidirectional Datatransmission," Sensors and Actuators A: Physical, vol. 115, Issues 2-3, Sep. 21, 2004, pp. 221-229, The 17th European Conference on Solid-State Transducers.

Claes, L.E., and Cunningham, J.L., "Monitoring the Mechanical Properties of Healing Bone," Clin Orthop Relat res (2009) 467:1964-1971.

Kao-Shang Shih, et al, "Influence of Muscular Contractions on the Stress Analysis of Distal Femoral Interlocking Nailing," Clinical Biomechanics, 23 (2008) 38-44.

Westerhoff, P., "An Instrumented Implant for in vivo Measurement of Contact Forcdes and Contact Moments in the Shoulder Joint," Medical Engineering & Physics, 31 (2009) 207-213.

Swedberg, Claire, "Surgeon Designs System to Monitor Orthopaedic Implants and Promote Healing," RFID Journal, reprinted from http://www.rfidjournal.com/article/articleprint13978/-1/1 on Mar. 26, 2008, 2 pages.

Rapp, Susan M., "Smart Implants to Provide Feedback, Measure Joint Loads, Detect Infection," Orthopedics Today, 2008, reprinted from http://www.orthosupersite.com/view.asp?rID=28657 on Jun. 6, 2008, 3 pages.

Seide, K., et al., "An Intelligent Internal Fixator System for Long Bones," 52nd Annual Meeting of the Orthopaedic Research Society, Paper No. 1698, Transactions vol. 31 Chicago, IL (2006) (with abstract search result printed from http://www.ors.org/abstract_search_result.asp on Mar. 8, 2011), 2 pages.

Rorie, J.F., et al, "A Telemetric Instrumentation System for Orthopaedic Implants," Apr. 19, 1995, 15 pages.

Arms, S.W., et al., "Wireless Strain Measurement Systems—Applications and Solutions," presented at NSF-ESF Joint Conference on Structural Health Monitoring, Strasbourg, France, Oct. 3-5, 2003.

Yang, G.Y., et al, "Design of Microfabricated Strain Gauge Array to Monitor Bone Deformation in Vitro and in Vivo," Proceedings of the Fourth IEEE Symposium on Bioinformatics and Bioengineering, May 19-21, 2004, 8 pages.

International Search Report issued in PCT/US2005/040052 on Jun. 22, 2006, 8 pages.

Written Opinion of the International Searching Authority issued in PCT/US2005/040052 on May 20, 2006, 9 pages.

International Preliminary Report on Patentability issued in PCT/US2005/040052 on May 8, 2007, 10 pages.

Einhorn, T.A., "The Cell and Molecular Biology of Fracture Healing," Clin Orthop, 1998: Suppl: 355:7-21.

Elvin, N., et al., "A Self-Powered Mechanical Strain Energy Sensor," Smart Matter Struct 2001; 10:1-7.

Kummer, F. J., et al., "Development of a Telemeterized Should Prosthesis," Clin Orthop Relat Res., Sep. 1996 (330):31-4.

Morris BA, D'Iima, D.D , J., Kovacevic, N., Arms, S.W., Townsend, C.P., and Colwell, C.W. Jr., "e-Knee: Evolution of the Electronic Knee Prosthesis," J Bone Joint Surg., 83:62-66, 2000.

Kaufman, K., Irby, S.E., and Colwell, C.W., "Instrumented Implant for Measuring Tibiofemoral Forces," J. Biomechanics, 29:667-671, 1996.

Taylor, S.J.G., Walker, P.S., Perry, J.S., Cannon, S.R., and Woledge, R., "The Forces in the Distal Femur and the Knee During Walking and Other Activities Measured by Telemetry," The Journal of Arthroplasty, 13:428-437, 1998.

SRI Consulting, "RFID Technologies", 2004; and Silicon Chip Online, "RFID Tags—How They Work." reprinted from http://www.siliconchip.com.au/cms/A30750/article.html.

Healthcare RFID Medical Microchip, Yenra, Apr. 30, 2003, reprinted from http://www.yenra.com/healthcare-rfid-medical-microchip/.

Verichip System, Product of VeriChip Corp., reprinted from http://www.verichipcorp.com/content/solutions/verichip reprinted on Apr. 26, 2011.

Sub-dermal RFID, Yenra, Sep. 25, 2003, reprinted from http://www.yenra.com/subdermalrfid/.

Clyde Church, "Radio Frequency Identification (RFID) Tracking of Orthopaedic Inventories Fact or Fiction, Today and Tomorrow," BONE Zone, Spring 2004, pp. 35-40.

Luis Figarella, Kirk Kikirekov, Heinrich Oehlmann, Radio Frequency Identification (RFID) in Health Care, Benefits, Limitations, Recommendations, A Health Industry Business Communications Council HIBCC White Paper (2006).

Alex Macario; Dean Morris; Sharon Morris "Initial Clinical Evaluation of a Handheld Device for Detecting Retained Surgical Gauze Sponges Using Radiofrequency Identification Technology" Arch Surg., 2006; 141:659-662.

Patricia Kaeding "RFID medical devices- Opportunities and challenges," Published Oct. 19, 2005, Wisconsin Technology Network, http://wistechnology.com.

First Office Action for Chinese Application No. 200680038574.1, mailed Oct. 9, 2009, 16 pages.

Second Office Action for Chinese Application No. 200680038574.1, mailed Jul. 7, 2011, 8 pages.

Communication pursuant to Article 94(3) EPC for EPO Application No. 07717657.6, mailed Jul. 12, 2011, 4 pages.

Final Office Action for U.S. Appl. No. 12/528,243, mailed Jan. 24, 2012, 11 pages.

Japanese Notice of Reasons for Rejection for Application No. 2008-528223 mailed Nov. 1, 2011 (English translation), 3 pages.

Chinese Decision on Rejection for Chinese Patent Application 200680038574.1 issued Oct. 26, 2011 (English translation), 12 pages.

International Preliminary Report on Patentable for International Application No. PCT/US20061033326, dated Feb. 26, 2008, 9 pages.

Written Opinion of the International Search Authority for International Application PCT/US2006/033326, mailed Feb. 23, 2008, 8 pages.

International Preliminary Report on Patentability for International Application No. PCT/US2009/032540, dated Aug. 3, 2010, 5 pages.

Written Opinion of the International Search Authority for International Application PCT/US2009/032540, dated Aug. 1, 2010, 4 pages.

Written Opinion of the International Search Authority for International Application PCT/US2008/075316, dated Mar. 6, 2010, 6 pages.

Office Action for U.S. Appl. No. 12/528,243, mailed Jun. 23, 2011, 10 pages.

Notice of Allowance for U.S. Appl. No. 12/064,546, mailed Dec. 27, 2011, 8 pages.

International Search Report for International Application PCT/US2009/032540 dated Apr. 29, 2009, 3 pages.

Global market for RFID in healthcare 2006-2016 by value: Source: IDTechEx, RFID in Healthcare 2006-2016, May 1, 2006.

Office Action for U.S. Appl. No. 12/528,243, mailed May 11, 2012.

* cited by examiner

CYCLE AND LOAD MEASUREMENT DEVICE

CROSS REFERENCE TO RELATED APPLICATION

This application claims priority to U.S. Provisional Patent Application Ser. No. 60/625,019 filed Nov. 4, 2004, the contents of which are incorporated herein by reference.

FIELD OF THE INVENTION

The present invention relates to a sensing system for an medical device and a method for evaluating a patient's compliance with a healing regimen, when the patient is provided with a medical device.

BACKGROUND

Orthopedic surgeons currently use X-rays to assess how patients with fractured limbs or ligament tears are progressing toward healing. X-rays unfortunately provide an incomplete picture for the surgeon. An X-ray will only provide an instantaneous picture of the fractured limb, for example. It will not provide the surgeon with information related to the amount of stress the patient has been placing on the fractured limb during the healing process. This additional information, if available, could assist the surgeon with their treatment decisions. For example, if a surgeon knows that a patient is putting too much load on the limb for a given fracture type, the surgeon could advise the patient to "take it easy" on the limb. Similarly, if the patient is not placing enough load on the limb, the surgeon can advise the patient as to the need for physical activity and/or physical therapy.

Moreover, if the patient has a surgical implant, an X-ray will not provide the surgeon with an indication of the amount of load that the patient has been putting on the implant. A surgeon armed with this information could evaluate the risk of implant failure and modify their treatment decisions accordingly.

Devices have previously been developed that attempt to provide a surgeon with more information regarding a patient's healing progress. For example, U.S. Pat. No. 6,034,296, issued Mar. 7, 2000 to Niell Elvin et al., is directed to an implantable bone strain telemetry sensing system and method. The system includes a strain sensor affixed to a bone fixing device. The sensor measures the strain in the bone fixing device by generating a strain signal in response to stress applied to the device. The strain sensor provides the strain data to an external receiver via wireless communications. The purpose of the system is to provide an indication of the extent of healing of a bone. The strain sensor is placed in a location such that it can measure strain on the fixation device. The patient is subjected to a series of exercises, and the strain on the fixation device is measured. It is expected that for a given stress level the strain on the fixation device will be reduced as the bone heals, as the bone will be able to absorb more of the stress.

The Elvin device is limited in the information it can provide to the surgeon. For example, as the bone heals, the device will provide less and less information to the surgeon—as discussed above, the strain sensor only registers data when the fixation device is stressed, and the amount of strain on the device will decrease as the bone heals. A sudden or unexpected increase in measured strain could indicate possible device failure or inadequate bone healing, but it will not provide an indication of the types or amount of stress that the patient has been applying to the implant, or whether the patient is following the surgeon's healing instructions. Nor does it provide an indication of whether the patient is putting enough or too much load on the injured limb. Moreover, one of the important features of the Elvin device is that it generates its own power by utilizing a piezoelectric-based material. These piezoelectric-based materials are complex and relatively costly.

Accordingly, there is a need for an improved device to address these shortcomings and provide surgeons with additional information to improve the healing assessment and assist with their treatment decisions.

SUMMARY

The present application relates to a sensing system for an medical device, the sensing system having at least one sensor for measuring movement of the medical device and a recording device for storing movement data from the at least one sensor. The application also relates to a method for evaluating a patient's compliance with a healing regimen, the patient provided with a medical device, the method having the steps of a) collecting movement data relating to movement of a sensing system affixed within, to, or near the medical device; b) retrieving the movement data from the sensing system; and c) analyzing the movement data and comparing the movement data to standard movement data to evaluate the patient's compliance with the healing regimen.

STATEMENT OF THE INVENTION

Accordingly, embodiments of the present invention provide for a sensing system for an medical device, characterized in that the sensing system comprises: at least one sensor for measuring movement of the medical device; and a recording device for storing movement data from the at least one sensor, in which the at least one sensor is an accelerometer.

More preferably, embodiments of the present invention provide for a sensing system in which the accelerometer is a discrete accelerometer and the recording device stores movement data from the discrete accelerometer when the discrete accelerometer detects an acceleration rate that exceeds a predetermined acceleration setpoint.

Yet even more preferably, embodiments of the present invention provide for a sensing system in which the setpoint of each at least one discrete accelerometer is from 0.25 to 100 $M/s^2$.

Also yet even more preferably, embodiments of the present invention provide for a sensing system in which the sensing system comprises at least a first discrete accelerometer and a second discrete accelerometer, and the first discrete accelerometer and the second discrete accelerometer have different acceleration setpoints.

Also more preferably, embodiments of the present invention provide for a sensing system in which additional data relating to the patient is storable in the sensing system, and the additional data is selected from the group consisting of patient height, patient weight, and patient surgical intervention information.

Also more preferably, embodiments of the present invention provide for a sensing system in which the sensing system further comprises a transmitter for wirelessly transmitting the stored movement data from the recording device to a receiver.

Also more preferably, embodiments of the present invention provide for a sensing system in which the medical device is an intramedullary nail, a bone plate, a bone screw, an external fixation device, a joint product, a trauma product, a spine product, or an interference screw.

Also more preferably, embodiments of the present invention provide for a sensing system in which the accelerometer is a continuous accelerometer, the continuous accelerometer detects movement data at a fixed cycle interval, and the recording device stores the movement data from the continuous accelerometer.

Even more preferably, embodiments of the present invention provide for a sensing system in which the cycle interval is from 0.01 to 1000 Hz.

Yet even more preferably, embodiments of the present invention provide for a sensing system in which the cycle interval is 32 Hz.

Embodiments of the present invention also provide for a method for evaluating a patient's compliance with a healing regimen, the patient provided with a medical device, characterized in that the method comprises: collecting movement data relating to movement of a sensing system affixed within, to, or near the medical device; retrieving the movement data from the sensing system; and analyzing the movement data and comparing the movement data to standard movement data to evaluate the patient's compliance with the healing regimen.

More preferably, embodiments of the present invention provide for a method for evaluating a patient's compliance with a healing regimen, in which the sensing system comprises at least one sensor for measuring movement of the medical device, and a recording device for storing movement data from the at least one sensor.

Even more preferably, embodiments of the present invention provide for a method for evaluating a patient's compliance with a healing regimen, in which the at least one sensor is a discrete accelerometer.

Yet even more preferably, embodiments of the present invention provide for a method for evaluating a patient's compliance with a healing regimen, in which the recording device stores movement data from the discrete accelerometer when the discrete accelerometer detects an acceleration rate that exceeds a predetermined acceleration setpoint.

Also yet even more preferably, embodiments of the present invention provide for a method for evaluating a patient's compliance with a healing regimen, in which the setpoint of the discrete accelerometer is from 0.25 to 100 m/s$^2$.

Also yet even more preferably, embodiments of the present invention provide for a method for evaluating a patient's compliance with a healing regimen, in which the sensing system comprises at least a first discrete accelerometer and a second discrete accelerometer, and the first discrete accelerometer and the second discrete accelerometer have different acceleration setpoints.

Even more preferably, embodiments of the present invention provide for a method for evaluating a patient's compliance with a healing regimen, in which the medical device is an intramedullary nail, a bone plate, a bone screw, an external fixation device, a joint product, a trauma product, a spine product, or an interference screw.

Also even more preferably, embodiments of the present invention provide for a method for evaluating a patient's compliance with a healing regimen, in which the at least one sensor is a continuous accelerometer, the continuous accelerometer detects movement data at a fixed cycle interval, and the recording device stores the movement data from the accelerometer.

Yet even more preferably, embodiments of the present invention provide for a method for evaluating a patient's compliance with a healing regimen, in which the cycle interval is from 0.01 to 1000 Hz.

Also yet even more preferably, embodiments of the present invention provide for a method for evaluating a patient's compliance with a healing regimen, in which the cycle interval is 32 Hz.

DETAILED DESCRIPTION

Figure 1:
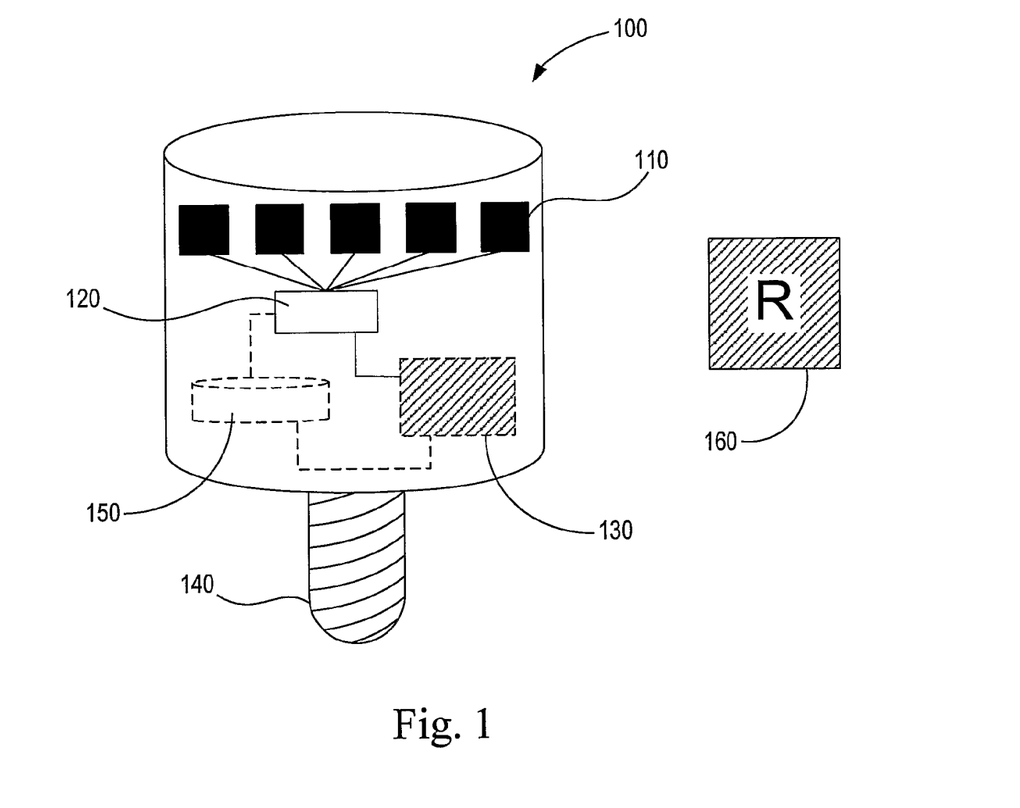
FIG. 1 is a schematic drawing of a preferred embodiment of the apparatus of the present invention.

FIG. 1 shows a sensing system 100 in accordance with a preferred embodiment of the present invention. In the configuration in FIG. 1, the sensing system 100 is configured and adapted to be affixed within a medical device (not shown), on the outside surface of the medical device, or on a surface near the medical device. The sensing system includes at least one sensor 110 for measuring movement of the medical device, a recording device 120 for storing movement data from the sensor 110, a transmitter 130 for wirelessly transmitting the stored movement data to a receiver 160, and a power source 150 for powering the sensing system 100. FIG. 1 depicts a preferred embodiment in which the sensing system is located within an intramedullary nail cap having a threaded portion 140. The sensing system is configured and adapted to be sealed within the nail cap, and the nail cap is thereafter screwed into an intramedullary nail (not shown), either before or after implantation of the intramedullary nail into a patient. In other embodiments, some or all of these features are unnecessary and/or are present in different configurations, positions, orientations, shapes and sizes.

As used herein, the term "medical device" refers to a device configured and adapted to be affixed to the body of a patient, either externally or internally, in order to support or immobilize any part of a patient's body. Examples of such medical devices include, for example, an intramedullary nail, a bone plate, a bone screw, an external fixation device, a joint product, a trauma product, a spine product, or an interference screw.

FIG. 1 depicts five sensors 110, although any number of sensors can be employed in the sensing system. Sensor 110 is an accelerometer. An accelerometer measures acceleration of an object. A known type of accelerometer employs a spring-mass damper system, which includes a spring attached to a mass. As a force is applied to the mass, the mass is displaced and the spring controls and limits the displacement. As one skilled in the art would understand, acceleration of the object can be calculated from this system. Accelerometers provide acceleration data in either a discrete time series or a continuous time series. As used herein, the term "discrete accelerometer" refers to an accelerometer providing data in a discrete time series, and the term "continuous accelerometer" refers to an accelerometer providing data in a continuous time series.

A discrete accelerometer can be provided with minimum and/or maximum acceleration setpoints. If an accelerometer is set with a minimum acceleration setpoint, it will not detect a cycle, e.g., a walking "step," unless the minimum threshold acceleration value is achieved. If the accelerometer is set with a maximum acceleration setpoint, it will only detect a cycle if the acceleration value is below the maximum setpoint. Thus, if a sensor utilizes multiple sensors with varying minimum and/or maximum acceleration setpoints, the types of forces which the sensor is subjected to can be quantified. Smaller forces can be detected by the accelerometers with the lower acceleration setpoints, and larger forces can be detected by the accelerometers with the higher acceleration setpoints.

Figure 2:
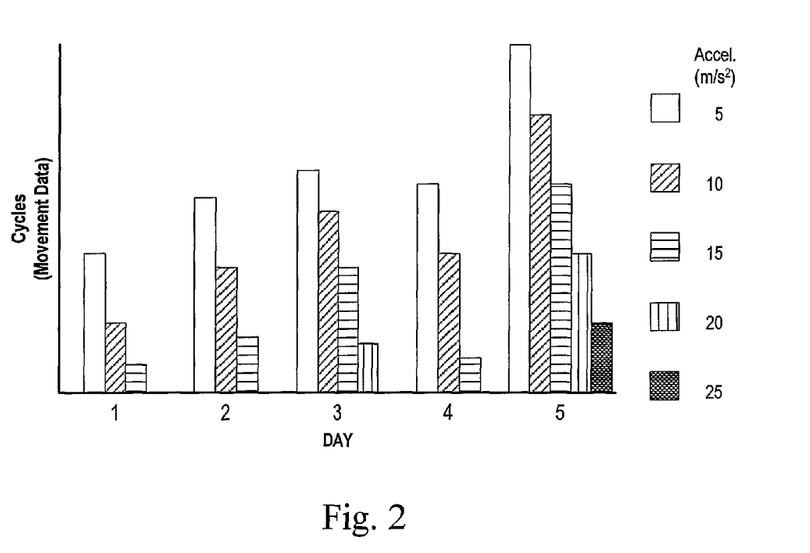
FIG. 2 is a graph illustrating prophetic raw data collected from a preferred embodiment of the apparatus of the present invention.

In a preferred embodiment, the sensing system 100 contains five discrete accelerometers 110, each with increasing minimum acceleration setpoints. A preferred range of acceleration setpoints is from 0.25 to 100 $m/s^2$. The graph illustrated in FIG. 2 depicts raw data that could be obtained over a five-day period from a sensing system with five accelerometers having minimum acceleration setpoints of 5, 10, 15, 20 and 25 $m/s^2$. The data provides several relevant pieces of information. For example, the first three days show a slow increase in a patient's activity, as indicated by an increase in the number of cycles/movement data recorded by the sensors. The activity is relatively light in the first two days, as only the 5, 10 and 15 $m/s^2$ sensors detect movement data. On Day 3, the 20 $m/s^2$ sensor detects its first data, indicating an increase in force applied to the sensor. Day 4 shows a decrease in activity, indicated by an overall decrease in cycles on the 5, 10 and 15 $m/s^2$ sensors and the lack of any data collected from the 20 $m/s^2$ sensor. Finally, Day 5 shows a relatively large increase in activity, with all five sensors measuring cycles in relatively greater amounts than the previous four days. A surgeon could compare this raw data to a standard, or expected, cycle distribution and determine whether the patient is engaging in too much or too little activity. The surgeon's diagnosis and treatment recommendations could then be adjusted accordingly.

It is understood that any number of discrete accelerometers can be used. A single discrete accelerometer with a low acceleration setpoint will adequately count the number of cycles that the sensor and medical device is subjected to. As discussed above, however, it is preferable that more than one discrete accelerometer is utilized in the sensing system, with each of the accelerometers having different acceleration setpoints. The different acceleration setpoints allow the cycles to be stratified based on impact load. Thus, by utilizing at least two discrete accelerometers, e.g., the surgeon can acquire more meaningful movement data. With at least two discrete accelerometers having different acceleration setpoints, the surgeon can quantify the types of loads, or forces, that the patient is putting on the medical device, which will help the surgeon diagnose and treat the patient.

Figure 3:
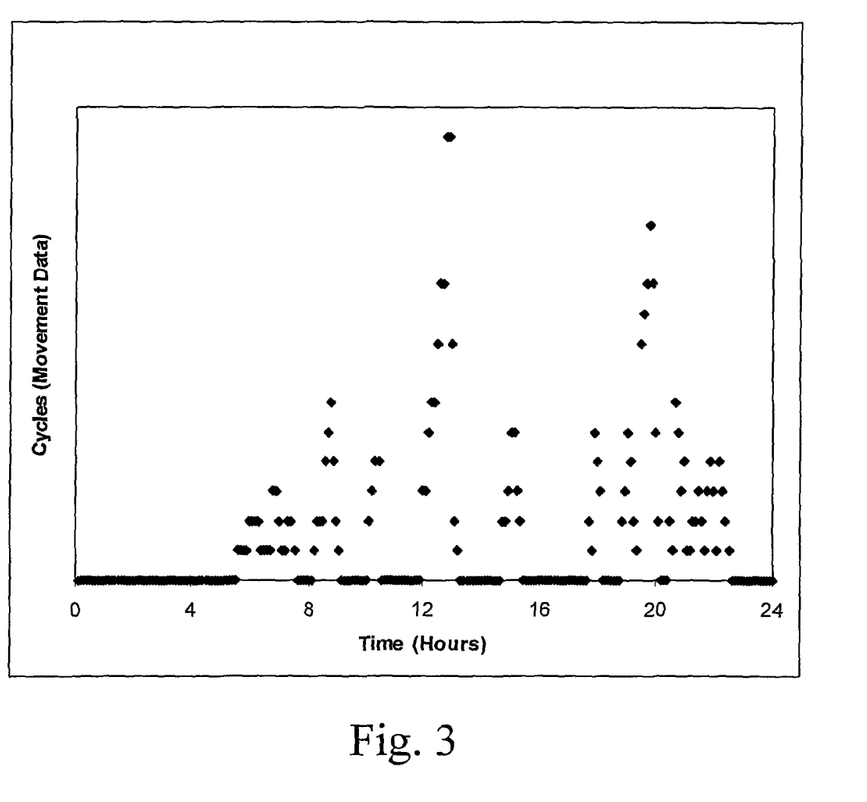
FIG. 3 is a graph illustrating prophetic raw data collected from another preferred embodiment of the apparatus of the present invention.

A continuous accelerometer measures and records acceleration of the sensor at a fixed cycle interval and can therefore provide an instantaneous acceleration reading. A preferred cycle interval is from 0.01 to 1000 Hz (cycles per second). More preferably, the continuous accelerometer measures and records acceleration data at a cycle interval of 32 Hz. Thus, a continuous accelerometer operating at a cycle interval of 32 Hz would detect movement data for the sensor 2,764,800 times in a 24-hour day (32 cycles/sec×60 sec/min×60 min/hr×24 hr/day). This movement data could be graphed as illustrated in FIG. 3. From this graph it can be seen that cycles peak at, e.g. lunchtime and dinnertime and are at a minimum in the evening and early morning hours. A surgeon could compare this raw data to a standard, or expected, cycle distribution and determine whether the patient is engaging in too much or too little activity. The surgeon's diagnosis and treatment recommendations could then be adjusted accordingly.

It is noted that because continuous accelerometers are rapidly measuring acceleration data, they could possibly capture undesirable background noise. This is not as much of a problem with discrete accelerometers, as discrete accelerometers can have minimum and maximum threshold acceleration setpoints, as discussed. As one skilled in the art would recognize, however, the problem of background noise in continuous accelerometers can be substantially minimized or eliminated with noise filters.

Figure 4:
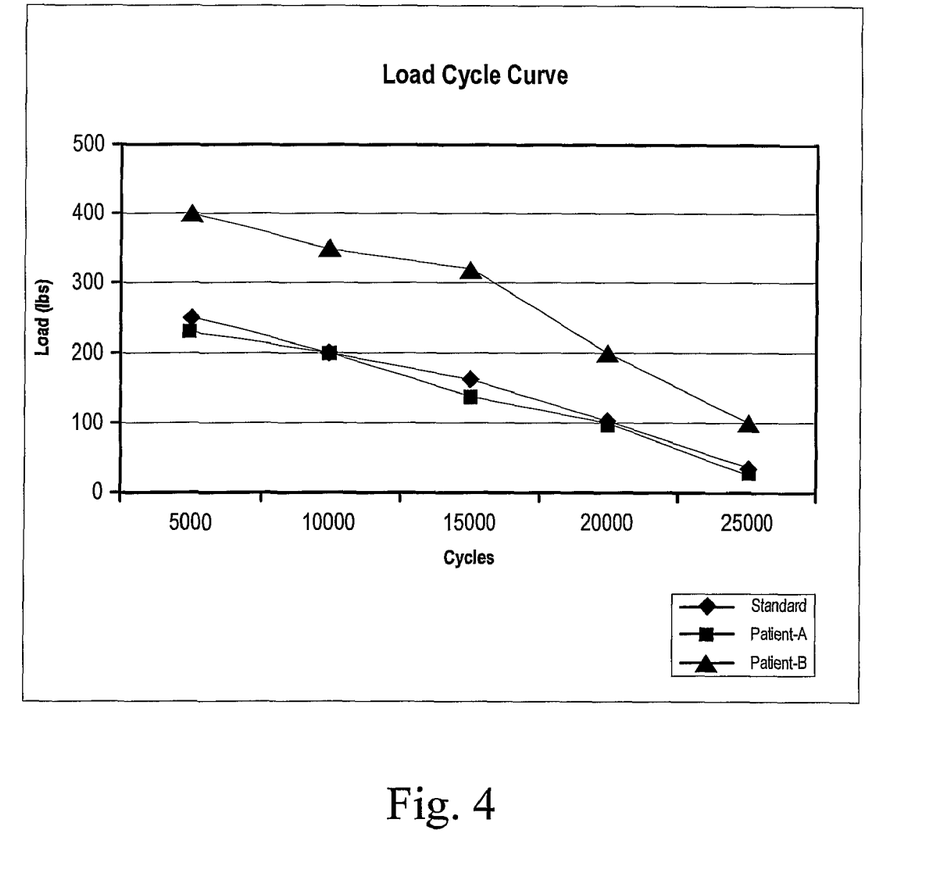
FIG. 4 is a graph illustrating a prophetic load cycle curve generated according to a preferred method of the present invention.
Figure 5:
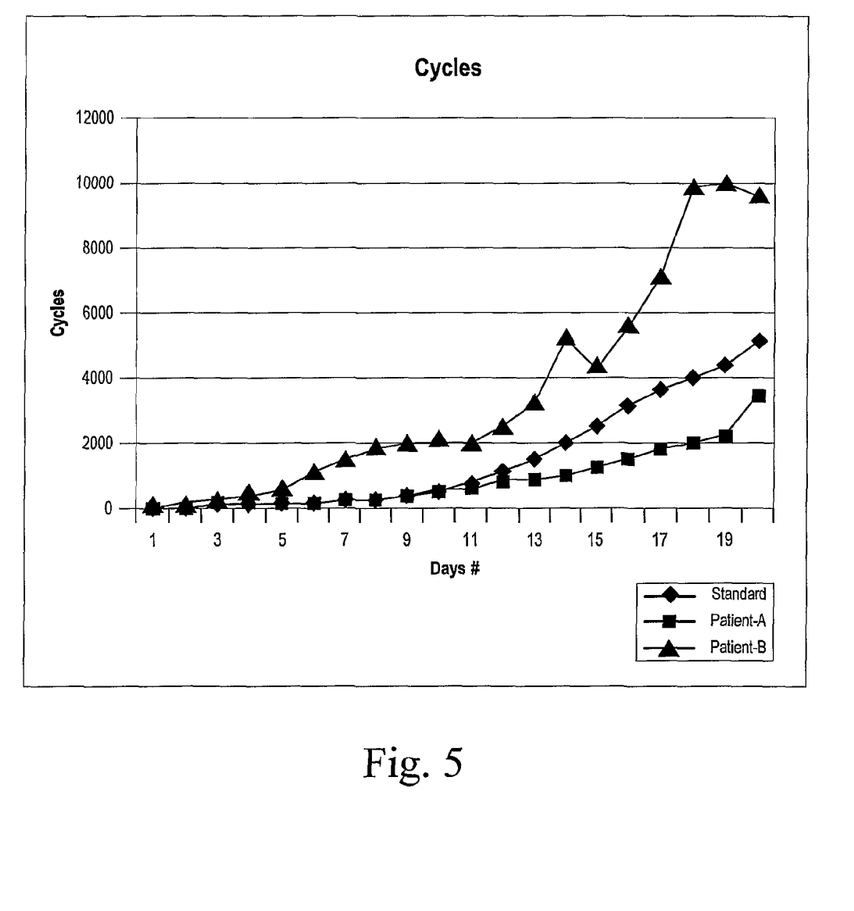
FIG. 5 is a graph illustrating a prophetic cycle curve generated according to a preferred method of the present invention.

Another possible method of displaying and evaluating the cycle/movement data is illustrated in FIGS. 4 and 5. FIG. 4 depicts a graph of load versus number of cycles, and includes data for five sensors. This graph includes data for two patients (A and B) as well as a standard curve. Because the sensors are set at different impact load thresholds a surgeon can determine the number of cycles the medical device has seen at each load. By comparing a patient's curve to a standard curve, a surgeon can determine whether or not the loading on the medical device is appropriate. From this curve, it is seen that Patient A's load curve closely tracks the standard curve and Patient A is therefore compliant. In contrast, it is seen that Patient B has placed too much load on the medical device and is non-compliant. Patient B could therefore expect problems with the life of the medical device if healing is not occurring.

FIG. 5 depicts a different method of displaying a patient's cycle data. This curve shows the number of cycles placed on the sensor (and medical device) each day over the course of a 20-day post-surgical healing regimen. As the patients heal, they become more mobile and exhibit an increasing trend of cycles per day. From this graph it is seen that Patient A is compliant with the standard, and, in fact, may actually not be putting enough cycles (and, accordingly, enough load) on the medical device and surgical site. In contrast, Patient B is non-compliant and has been placing too many cycles (and too much load) on the medical device. It is also seen that Patient B's activity peaks well above the standard at Day 14 and Days 18-20. The ability for surgeons to track compliance in this manner is valuable in modifying the treatment protocol of a patient during healing.

Turning back to the sensing system of FIG. 1, recording device 120 stores cycle/movement data from the sensor(s) 110. The recording device can be any type of computer recording media, which includes, but is not limited to, RAM, ROM, EPROM, EEPROM, flash memory or other solid-state memory technology, CD-ROM, digital versatile disks ("DVD") or other optical storage, magnetic cassettes, magnetic tape, magnetic disk storage or other magnetic storage devices, or any other medium which can be used to store the movement data. It is understood that data storage and physical size considerations are factors to be considered in the selection of the recording device.

It is also understood that the sensing system can store additional patient data, such as patient height, patient weight, and patient surgical intervention information. This information can be used with the stored movement data to facilitate processing of the medical device load information, as described above. The additional patient information can be stored in recording device 120 or in a separate memory storage device.

Transmitter 130 is configured and adapted to wirelessly transmit the stored cycle/movement data to receiver 160. Any type of wireless technology can be used to transmit the stored data to the receiver, including RF, UHF, VHF, Bluetooth, 802.11, ZigBee, and any other technologies suitable for wireless transmission of data.

Power source 150 powers the sensing system components 100, and can be any suitable portable source of power including a battery, piezoelectric power generation unit, capacitor, and kinetic power generation unit. As with the recording device, it will be recognized by one skilled in the art that selection of power source type will depend on system power requirements and physical size considerations.

As discussed, sensing system 100 is configured and adapted to be affixed within a medical device, on the outside surface of the medical device, or on a surface near the medical device. In a preferred embodiment, the sensing device is manufactured inside an intramedullary nail cap and screwed into an intramedullary nail at threaded portion 140. The nail cap is manufactured from a suitable medical-grade material such as stainless steel and alloys thereof, titanium and alloys thereof, cobalt chrome, composite material, or polymer material. The nail cap is hollow with an opening to allow insertion of the sensing system. The inside of the nail cap is instrumented with the sensing system as described herein. A lid is placed over the opening in the nail cap, and the lid is sealed to prevent ingress of bodily fluids. The lid can be sealed by any known means for providing an inert atmosphere inside the nail cap, such as welding, adhesives, and O-rings.

In other embodiments, the sensing system could be placed in a washer that could be fastened to a bone near a bone plate. Alternatively, the washer could be fastened directly to the bone plate. The sensing system could also be added to an external fixation device, and could even be added to an interference screw used for treating a ligament tear.

Although specific examples of applications for the sensing system according to the present application are described herein, it is understood that the sensing system can be utilized in any type of medical device, including, but not limited to, an intramedullary nail, a bone plate, a bone screw, an external fixation device, a joint product, a trauma product, a spine product, or an interference screw.

While this invention has been described in detail with particular reference to the disclosed embodiments, it will be understood that variations and modifications can be affected within the spirit and scope of the invention as described herein and as defined in the appended claims.

That which is claimed:

1. A method for evaluating a patient's compliance with a bone healing regimen, the patient provided with a medical device, the method comprising:
   collecting movement data relating to movement of a sensing system affixed within, to, or near the medical device;
   retrieving the movement data from the sensing system;
   analyzing the movement data to determine cycle counts for one or more acceleration levels for each of a plurality of time periods; and
   evaluating the patient's compliance with the bone healing regimen by comparing the cycle counts to a standard cycle distribution comprising a plurality of standard cycle counts that have predetermined values that indicate a different number of cycles for at least some of the plurality of time periods.

2. The method of claim 1, in which the sensing system comprises at least a first discrete accelerometer and a second discrete accelerometer, and the first discrete accelerometer and the second discrete accelerometer have different acceleration setpoints, and in which the sensing system comprises a recording device for storing movement data from the first discrete accelerometer and the second discrete accelerometer.

3. The method of claim 2, in which at least one of the acceleration setpoints is a maximum acceleration setpoint defined such that a cycle is detected if a measured acceleration is below the maximum setpoint.

4. The method of claim 2, in which at least one of the acceleration setpoints is a minimum acceleration setpoint.

5. The method of claim 2, in which the recording device stores movement data from the first discrete accelerometer when the first discrete accelerometer detects an acceleration rate that exceeds one of the acceleration setpoints.

6. The method of claim 5, in which the acceleration setpoint of the first discrete accelerometer or the acceleration setpoint of the second discrete accelerometer is from 0.25 to 100 m/s$^2$.

7. The method of claim 1, in which the medical device is an intramedullary nail, a bone plate, a bone screw, an external fixation device, a joint product, a trauma product, a spine product, or an interference screw.

8. The method of claim 1, in which the sensing system is located within an intramedullary nail cap.

9. The method of claim 1, wherein analyzing the movement data to identify cycle counts for one or more acceleration levels comprises analyzing the movement data to identify cycle counts for a plurality of different acceleration levels.

10. The method of claim 1, wherein evaluating the patient's compliance with the bone healing regimen by comparing the cycle counts to the standard cycle distribution comprises comparing the cycle counts to a standard cycle distribution indicating a number of cycles at each of a plurality of load levels.

11. The method of claim 1, wherein the standard cycle distribution corresponds to the bone healing regimen and indicates, for the plurality of time periods, numbers of cycles that increase with time.

12. The method of claim 1, wherein the bone healing regimen is a post-surgical bone healing regimen.

13. The method of claim 1, wherein evaluating the patient's compliance with the bone healing regimen by comparing the cycle counts to the standard cycle distribution comprises determining whether the patient's activity level is compliant.

14. The method of claim 1, wherein collecting movement data relating to movement of a sensing system affixed within, to, or near the medical device comprises collecting movement data relating to movement of a sensing system affixed within, to, or near the medical device, the sensing system comprising a continuous accelerometer configured to detect movement data at a fixed cycle interval.

15. The method of claim 1, wherein collecting movement data relating to movement of a sensing system affixed within, to, or near the medical device comprises collecting movement data relating to movement of a sensing system affixed within, to, or near the medical device, the sensing system comprising at least a first discrete accelerometer and a second discrete accelerometer, the first discrete accelerometer and the second discrete accelerometer having different acceleration setpoints; and
   wherein analyzing the movement data to determine cycle counts for one or more acceleration levels comprises analyzing the movement data to determine cycle counts for a plurality of acceleration levels, each of the plurality of acceleration levels corresponding to one of the acceleration setpoints.

16. The method of claim 1, wherein the medical device is externally affixed to the patient's body.

17. The method of claim 1, wherein collecting movement data relating to movement of a sensing system affixed within, to, or near the medical device comprises applying one or more noise filters to reduce noise in acceleration data measured by the sensing system.

18. The method of claim 1, further comprising depicting the detected cycle counts and the standard cycle counts of the standard cycle distribution in a graph.

19. The method of claim 1, wherein the sensing system stores patient data comprising one or more of patient height, patient weight, and patient surgical intervention information.

20. The method of claim 1, wherein the sensing system is located within a washer configured to be attached to a bone or to a bone plate.

21. The method of claim 1, wherein the sensing system comprises a plurality of sensors having different setpoints, the different setpoints varying by substantially equal increments.

22. The method of claim 1, wherein the medical device is an orthopaedic support or immobilization device.

23. The method of claim 1, wherein the cycle counts define a patient curve and the predetermined standard cycle counts define a standard curve,
wherein comparing the cycle counts to the standard cycle distribution comprises comparing the patient curve with the standard curve.

24. The method of claim 23, wherein evaluating the patient's compliance with the bone healing regimen comprises assessing a degree to which the patient curve tracks the standard curve.

25. A method for evaluating a patient's compliance with a bone healing regimen, the patient provided with a medical device, the method comprising:
collecting movement data relating to movement of a sensing system affixed within, to, or near the medical device, the sensing system comprising at least a first discrete accelerometer for measuring movement of the medical device and a second discrete accelerometer for measuring movement of the medical device, the first discrete accelerometer and the second discrete accelerometer having different acceleration setpoints;
retrieving the movement data from the sensing system;
analyzing the movement data to determine, for each of a plurality of time periods, detected cycle counts for movements corresponding to the different acceleration setpoints; and
evaluating the patient's compliance with the bone healing regimen by comparing the detected cycle counts for the plurality of time periods to a standard cycle distribution indicating a predetermined set of standard cycle counts corresponding to the plurality of time periods, the standard cycle distribution indicating different standard cycle counts for at least some of the plurality of time periods,
in which the sensing system comprises a recording device for storing movement data from the first discrete accelerometer and the second discrete accelerometer, and the recording device stores movement data from the first discrete accelerometer and the second discrete accelerometer.

26. The method of claim 25, in which at least one of the acceleration setpoints is from 0.25 to 100 m/s$^2$.

27. The method of claim 25, in which the medical device is an intramedullary nail, a bone plate, a bone screw, an external fixation device, a joint product, a trauma product, a spine product, or an interference screw.

28. The method of claim 25, in which at least one of the acceleration setpoints is a maximum acceleration setpoint defined such that a cycle is detected if a measured acceleration is below the maximum setpoint.

29. The method of claim 25, in which at least one of the acceleration setpoints is a minimum acceleration setpoint.

30. The method of claim 25, in which the sensing system is located within an intramedullary nail cap.

31. The method of claim 25, wherein the standard cycle counts indicate preset levels of activity that comply with the post-surgical bone healing regimen at corresponding time periods during the post-surgical bone healing regimen.

32. A method for evaluating a patient's compliance with a bone healing regimen, the patient provided with a medical device, the method comprising:
collecting movement data relating to movement of a sensing system affixed within, to, or near the medical device;
retrieving the movement data from the sensing system;
analyzing the movement data to determine cycle counts for a plurality of different acceleration levels; and
evaluating the patient's compliance with the bone healing regimen by comparing the cycle counts to a standard cycle distribution corresponding to the bone healing regimen, wherein the standard cycle distribution defines a predetermined curve indicating expected activity levels at different time periods during the bone healing regimen, and the standard cycle distribution indicates a different number of cycles for each of a plurality of time periods.

33. The method of claim 32, wherein the standard cycle counts indicated by the standard cycle distribution include standard cycle counts for each of multiple consecutive days.

34. The method of claim 32, wherein the plurality of time periods include three or more consecutive days, and the standard cycle distribution indicates different standard cycle counts for each of the three or more consecutive days.

35. A method for evaluating a patient's compliance with a post-surgical bone healing regimen, the patient having an implanted intramedullary nail, the method comprising:
collecting movement data relating to movement of a sensing system located within the intramedullary nail or an intramedullary nail cap coupled to the intramedullary nail, the sensing system comprising at least a first discrete accelerometer for measuring movement of the patient and a second discrete accelerometer for measuring movement of the patient, the first discrete accelerometer and the second discrete accelerometer having different acceleration setpoints;
analyzing the movement data to determine, for each of a plurality of time periods, detected cycle counts for movements corresponding to the different acceleration setpoints; and
evaluating the patient's compliance with the post-surgical bone healing regimen by comparing the detected cycle counts for each of the plurality of time periods with a standard cycle distribution comprising a collection of predetermined standard cycle counts that represent preset levels of activity that comply with the post-surgical bone healing regimen at corresponding time periods during the post-surgical bone healing regimen, the predetermined standard cycle counts having different cycle count values for at least some of the plurality of time periods.

36. The method of claim 35, wherein the standard cycle distribution defines a predetermined standard curve that spans the plurality of time periods and indicates predetermined trends in the levels of activity that comply with the post-surgical bone healing regimen during the post-surgical bone healing regimen.

37. The method of claim 36, wherein the cycle counts over the plurality of time periods define a patient curve that spans the plurality of time periods, wherein comparing the cycle counts for the plurality of time periods with the standard cycle distribution comprises comparing the patient curve for the plurality of time periods with portions of the predetermined standard curve corresponding to the plurality of time periods.

38. The method of claim 37, wherein evaluating the patient's compliance with the bone healing regimen comprises assessing a degree to which the patient curve tracks the predetermined standard curve.

39. The method of claim 36, wherein the standard cycle distribution defines a patient-independent standard trend curve that indicates expected activity levels during the healing regimen.

40. The method of claim 39, wherein the patient-independent standard trend curve indicates expected activity levels over the course of the entire post-surgical bone healing regimen.

41. The method of claim 35, wherein the plurality of time periods include three or more consecutive days, and the standard cycle distribution includes different standard daily cycle counts for each of the three or more consecutive days.

* * * * *